United States Patent [19]
Hansen

[11] Patent Number: 5,279,290
[45] Date of Patent: Jan. 18, 1994

[54] THERMAL RECOVERY HEATING UNIT

[75] Inventor: William J. Hansen, Hales Corners, Wis.

[73] Assignee: Enthermics Medical Systems, Menomonee Falls, Wis.

[21] Appl. No.: 976,679

[22] Filed: Nov. 16, 1992

Related U.S. Application Data

[63] Continuation of Ser. No. 666,089, Mar. 7, 1991, abandoned.

[51] Int. Cl.$^5$ ............................................. A61F 7/00
[52] U.S. Cl. ..................................... 607/98; 607/112
[58] Field of Search ............................... 128/373, 402

[56] References Cited

U.S. PATENT DOCUMENTS

| | | | |
|---|---|---|---|
| 959,743 | 5/1910 | Hoyt | 128/367 X |
| 1,643,399 | 9/1927 | Wentworth | 128/33 X |
| 1,968,015 | 7/1934 | Cooke et al. | 128/373 |
| 2,184,418 | 12/1939 | Faigle | 128/373 |
| 2,203,263 | 6/1940 | Honsaker | 128/373 |
| 2,437,016 | 3/1948 | Christensen | 128/402 X |
| 2,579,964 | 12/1951 | Reynolds | 128/373 X |
| 2,756,754 | 7/1956 | Poffenbarger | 128/373 |
| 2,960,986 | 11/1960 | Gibbons | 128/373 |
| 3,741,218 | 6/1973 | Novak | 128/373 |
| 4,033,354 | 7/1977 | DeRosa | 128/402 X |
| 4,501,275 | 2/1985 | Maahs | 128/402 |
| 4,739,763 | 4/1988 | Parsell | 128/373 X |

Primary Examiner—William H. Grieb
Attorney, Agent, or Firm—Andrus, Sceales, Starke & Sawall

[57] ABSTRACT

A radiant heating unit for treating patients suffering from hypothermia is adapted to be used with a standard stretcher so that the patient may be moved into and removed from the device without moving the patient from one support surface to another. The unit includes an enclosure for defining a chamber into which the patient may be inserted. A guard is placed between the patient and the heated surfaces of the enclosure to protect the patient against direct contact with the heated surface of the enclosure.

15 Claims, 5 Drawing Sheets

FIG. 3

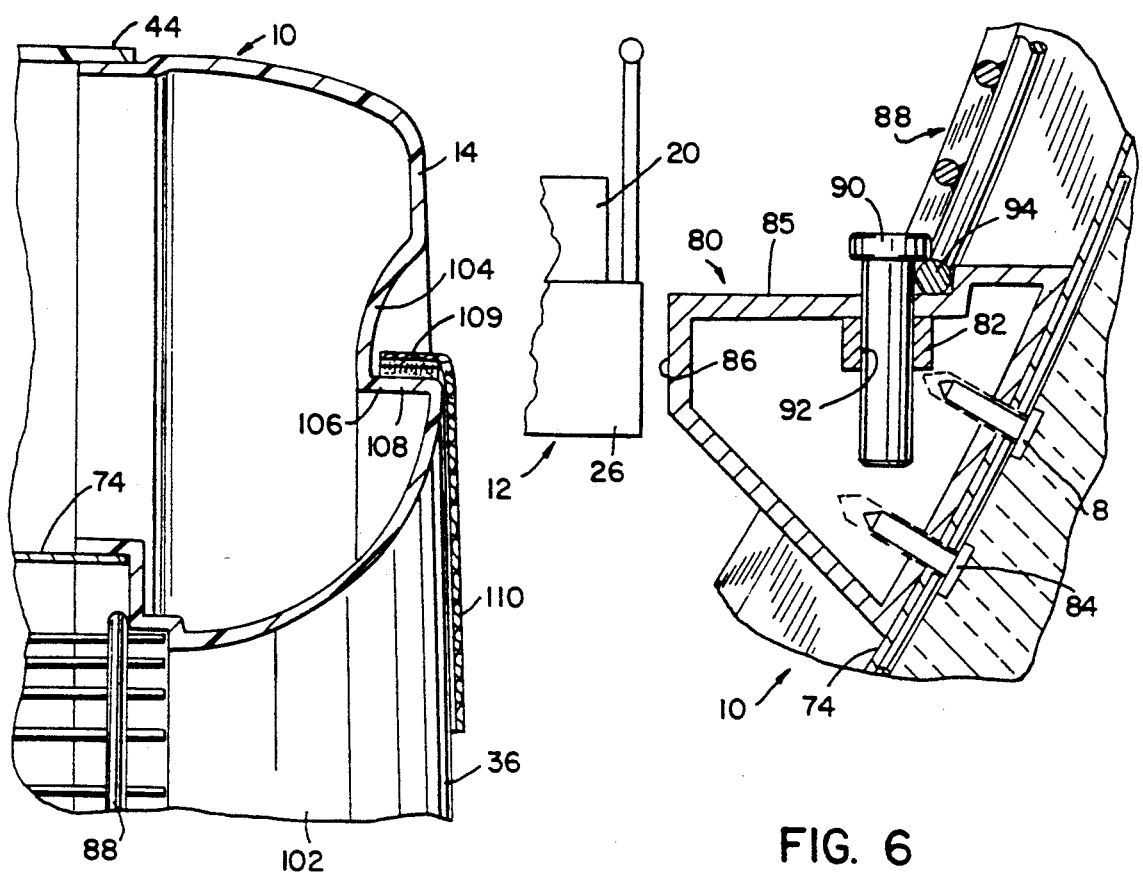
FIG. 5
FIG. 6
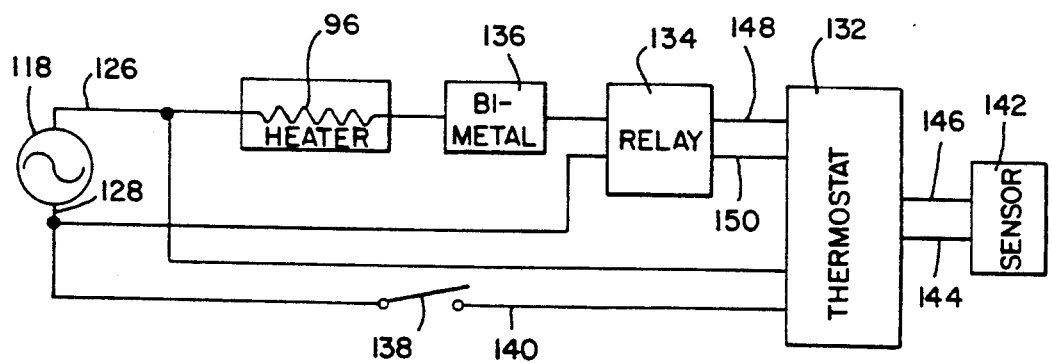
FIG. 7

THERMAL RECOVERY HEATING UNIT

This application is a continuation of Ser. No. 07/666,089, filed Mar. 7, 1991 now abandoned.

BACKGROUND OF THE INVENTION

1. Field of the Invention

The subject invention is directed to elevating the core body temperature of a human being and is specifically directed to a radiant heating surface for elevating the temperature of a patient suffering from hypothermia.

2. Description of the Prior Art

Thermal recovery devices of the type used for elevating the temperature of human beings are well known. For example, U.S. Pat. No. 2,579,964 issued to J. L. Reynolds on Dec. 25, 1991 discloses a heating unit which is adapted to be mounted directly on the frame of a bed and defines a hood for enveloping the patient. Heat is applied to the surface of the hood. By design, the hood is in close proximity to the extremities of the patient, particularly the arms and legs. If the patient moves or extends his extremities during treatment, there is a risk of thermal injury caused by direct contact with the heated surface of the recovery unit.

U.S. Pat. No. 2,184,418 issued to A. A. Faigle on Dec. 26, 1939 discloses a heating unit which includes a sectioned hood permanently attached to a massage table, where in both the hood and the table contain heating elements for warming the patient. The surface temperature is limited since the patient is in direct contact with a heated surface on the table. In addition, the Faigle design requires that the patient be moved from one surface to another since the table is a permanent part of the device and is not possible. Further, the table is not readily suited for any use other than heat treatment. U.S. Pat. No. 2,960,986 issued to B. F. Gibbons on Nov. 22, 1960 is an improved therapeutic heat and massage table, similar to that disclosed in Faigle. As in Faigle, a specifically designed table is required for use of the unit. Gibbons utilizes light bulbs as the heating element.

U.S. Pat. No. 3,741,218 issued to K. Novak on Jun. 26, 1973 also discloses a heat therapy apparatus using light bulbs as the heating elements for a hood. The Novak device also requires a specially designed table for supporting the hood, requiring that the patient be moved from another surface onto the table for treatment. As with Reynolds, the Novak device does not provide any means for protecting the patient from direct contact with the hood during treatment.

U.S. Pat. No. 1,643,399 issued to M. W. Wentworth on Sep. 27, 1927, and U.S. Pat. No. 959,743 issued to J. C. Hoyt on May 31, 1910, discloses hooded units which include a drape for closing the open end of the unit for enveloping the body of the patient during treatment.

U.S. Pat. No. 1,968,015 issued to W. H. Cooke et al on Jul. 31, 1934, and U.S. Pat. No. 2,437,016 issued to H. E. Christensen on Mar. 2, 1948 discloses therapeutic heating devices which may be placed either on the patient's bed or a standard table for heating extremities or a portion of the patient's body. Neither of these devices provide for protection of the patient from direct contact with the heating elements or heated surfaces during treatment.

U.S. Pat. No. 4,501,275 issued to J. D. Maahs on Feb. 26, 1985 discloses a closed heating unit for elevating the core body temperature of mammals to a hyperthermic condition for treatment of cancer of the like. The Maahs device is self-contained and requires movement of the patient from another device in order to place the patient in the unit for treatment.

All of the devices of the prior art have shortcomings in that they either are not self-contained or, where they are self-contained, require that the patient be moved from a separate apparatus onto the unit for treatment. As with all medical procedures, during the critical stages of treatment, it is desired to move the patient as little as necessary. Further, the units of the prior art do not provide means for elevating the body temperature by a radiant heating technique while protecting the patient from accidental contact with the heated surfaces of the patient chamber, increasing the risk of thermal injury to the patient during treatment.

SUMMARY OF THE INVENTION

The subject invention overcomes the shortcomings of the prior art. It is self-contained and portable yet accommodates a standard stretcher, whereby the patient may be moved into the device for treatment without moving the patient from one apparatus to another. The radiant heating unit of the subject invention includes a cylindrical heating chamber with heat applied directly to and radiating outwardly from the interior, peripheral surface of the chamber. A protective grid is placed between the patient and the heated surface to protect the patient against accidental thermal injury during treatment.

Thermal blankets are used to enclose the patient within the cylindrical chamber to increase the efficiency of the unit. Other treatments and procedures may be performed on the patient during treatment in the unit and the patient may be readily and easily moved into and out of the unit without requiring movement from one apparatus to another.

The thermal recovery heating unit of the subject invention has been found to be particularly useful in treating a patient suffering from environment induced hypothermia and/or for elevating a patient from a lowered core body temperature which has been induced for certain surgical procedures. The unit permits elevation of the body core temperature to the desired level in a controlled environment using a radiant heating chamber which eliminates the need for direct contact with the heated surfaces or the heating elements, reducing the risk of thermal injury to the patient during treatment.

It is, therefore, an object and feature of the subject invention to provide for a radiant heating unit for treating a patient suffering from hypothermia by elevating his core body temperature to desired levels in an accelerated manner in a safe environment.

It is also an object and feature of the subject invention to permit treatment of the patient without removing him from the apparatus or device upon which he is located prior to treatment.

It is a further object and feature of the subject invention to provide for a thermal recovery heating unit which may be used while the patient is undergoing other treatments and procedures such as, by way of example, hemodialysis and the like.

Other objects and features of the invention will be readily apparent from the drawing and detailed description of the preferred embodiment, which follow.

BRIEF DESCRIPTION OF THE DRAWING

FIG. 3 is a top elevational view, partially in section, of the unit shown in FIG. 1.

FIG. 5 is an enlarged fragmentary view looking generally in the direction of FIG. 1.

FIG. 6 is an enlarged fragmentary view looking generally in the direction of FIG. 2.

FIG. 7 is a schematic diagram of an electrical control circuit for the thermal recovery heating unit of the subject invention.

DETAILED DESCRIPTION OF THE PREFERRED EMBODIMENT

The thermal recovery heating unit of the subject invention is a radiant heat device used for thermal recovery of patients who are hypothermic. The lowered body core temperature may be due to environmental exposure or medically induced for various surgical procedures. The thermal recovery heating unit is non-invasive and is adapted for ready use by recovery nurses or other technical personnel. The unit is advantageous in that it permits the initiation of therapy immediately, without lengthy patient preparation, and permits monitoring of the patient's blood pressure, ECG rhythm and other vital signs during use. The radiant heating design of the system minimize the potential of thermal injury to the skin and avoid peripheral vasodilatation by keeping the skin temperature modest. Various other procedures may be performed on the patient during treatment such as, by way of example, hemodialysis and the like.

Figure 1:
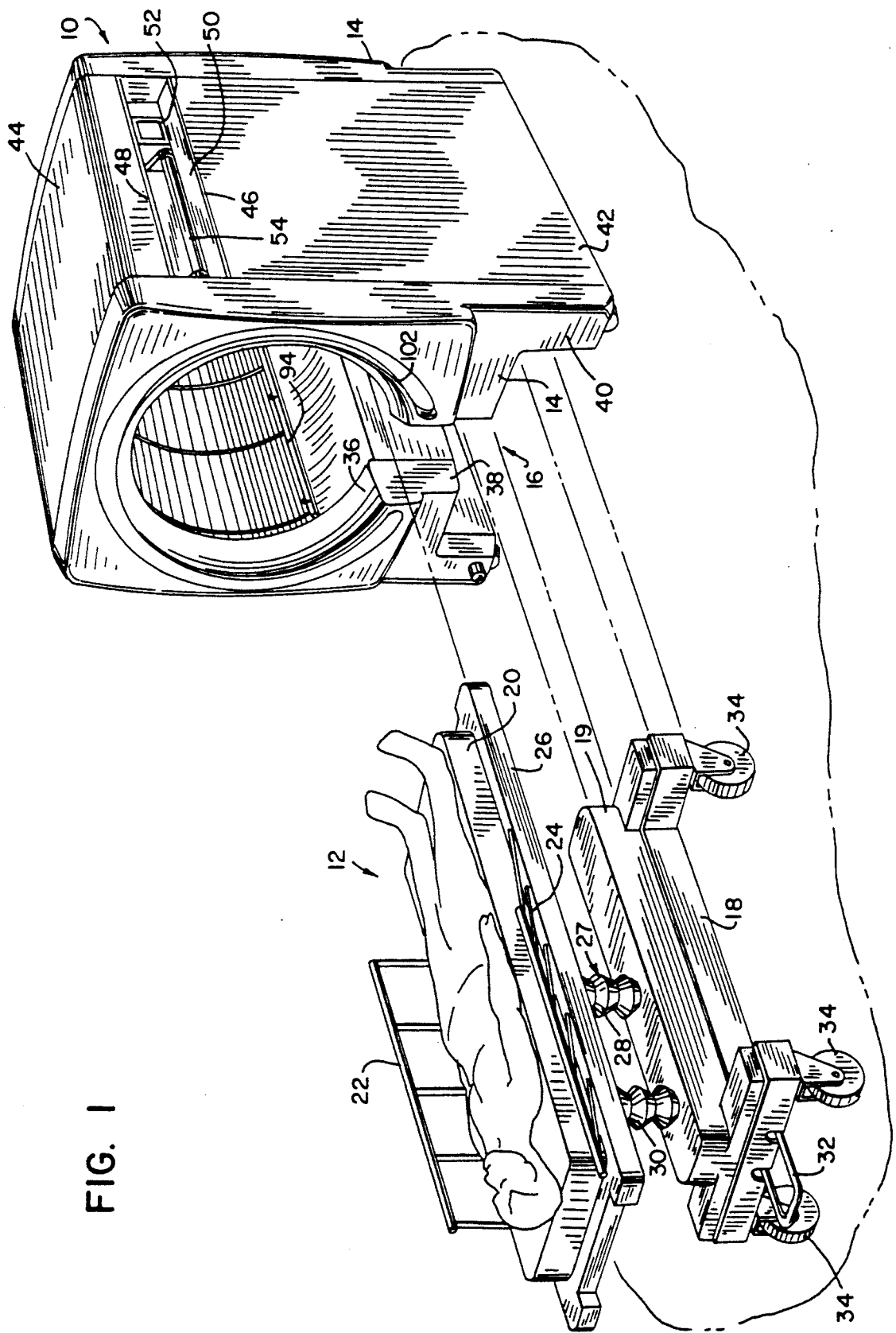
FIG. 1 is a perspective view of a thermal recovery heating unit in accordance with the subject invention.

As shown in FIG. 1, the heating unit 10 is adapted to be used with a standard hospital stretcher 12. The front end panel 14 of the heating unit 10 includes a key hole opening 16 adapted to receive the stretcher 12 without interference. In the preferred embodiment, a standard stretcher model number 919, manufactured by Stryker Medical Products, is used, with the base cover 18 being modified to clear the key hole opening in the end panel 14 of the unit. The patient pad 20 is the standard pad supplied with the stretcher. The guide rails 22, 24 are covered with a heat resistant coating to maintain the guide rails at a relatively cool temperature to minimize the risk of thermal injury to the patient during treatment. The stretcher bed 26 is supplied on an elevator system 27. Specifically, the bed is pivotally supported on a center post (not shown) enclosed in the bellows 28. A manually operable elevator is secured to the bed 26 and the base 18 and is enclosed in the bellows 30. The elevator actuator 32 may be used to tilt the bed 26 to place the patient in an inclined position, as is desirable for certain types of treatment. The preferred embodiment of the unit 10 is designed to accommodate the stretcher 12 in its horizontal position. As is common, the stretcher 12 includes a plurality of rollers or wheels 34.

Figure 2:
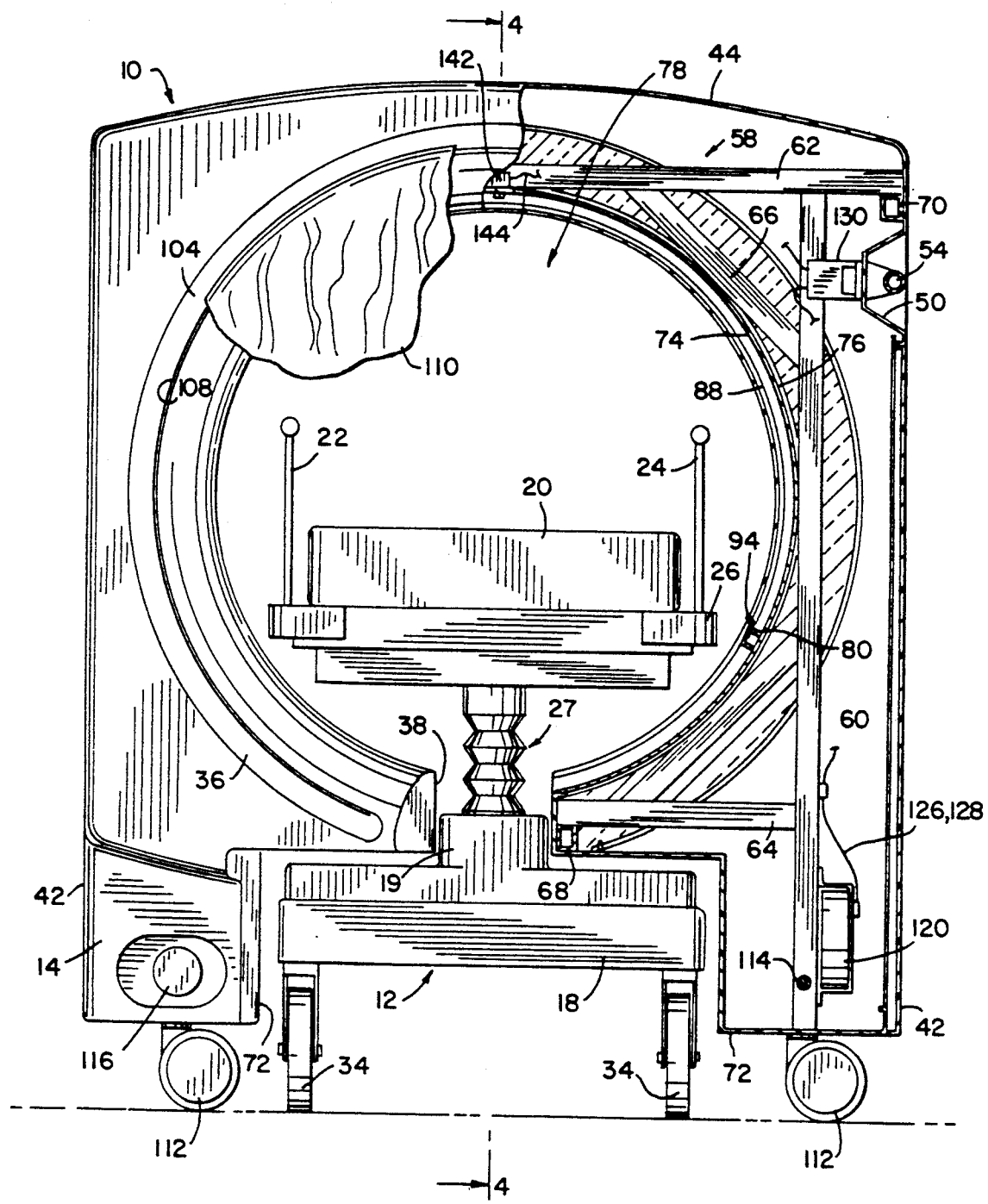
FIG. 2 is a front elevational view, partially in section, of the unit shown in FIG. 1.

The thermal recovery heating unit 10 includes identical end panels 14 at its front and back. Each end panel 14 includes the key hole opening 16 which is adapted to receive the stretcher 12 in a nested relationship, as best shown in FIG. 2. The enlarged circular portion 36 of the opening 16 easily accommodates the patient with ample clearance on all sides. The narrow slotted portion 38 of the opening 16 is adapted to accommodate the elevator assembly 27 and the upper portion 19 of the cover 18 of the stretcher. The enlarged rectangular slotted portion 40 of the opening 16 accommodates the lower base and the wheels of the stretcher.

In the preferred embodiment, the outer shell of the heating unit includes a pair of rectangular side panels 42 and an upper wrap around top panel 44. The side panels 42 and top panel 44 have spaced apart parallel edges 46 and 48, respectively, for accommodating a handle and/or control panel inset 50. The control panel 52 is mounted in the panel 50, as shown in FIG. 1. Panel 50 also accommodates a bar handle 54 which is mounted to the insert panel 50 in typical fashion. A similar handle is mounted in the insert panel 50 on the opposite side of the unit for facilitating in movement of the unit.

Figure 4:
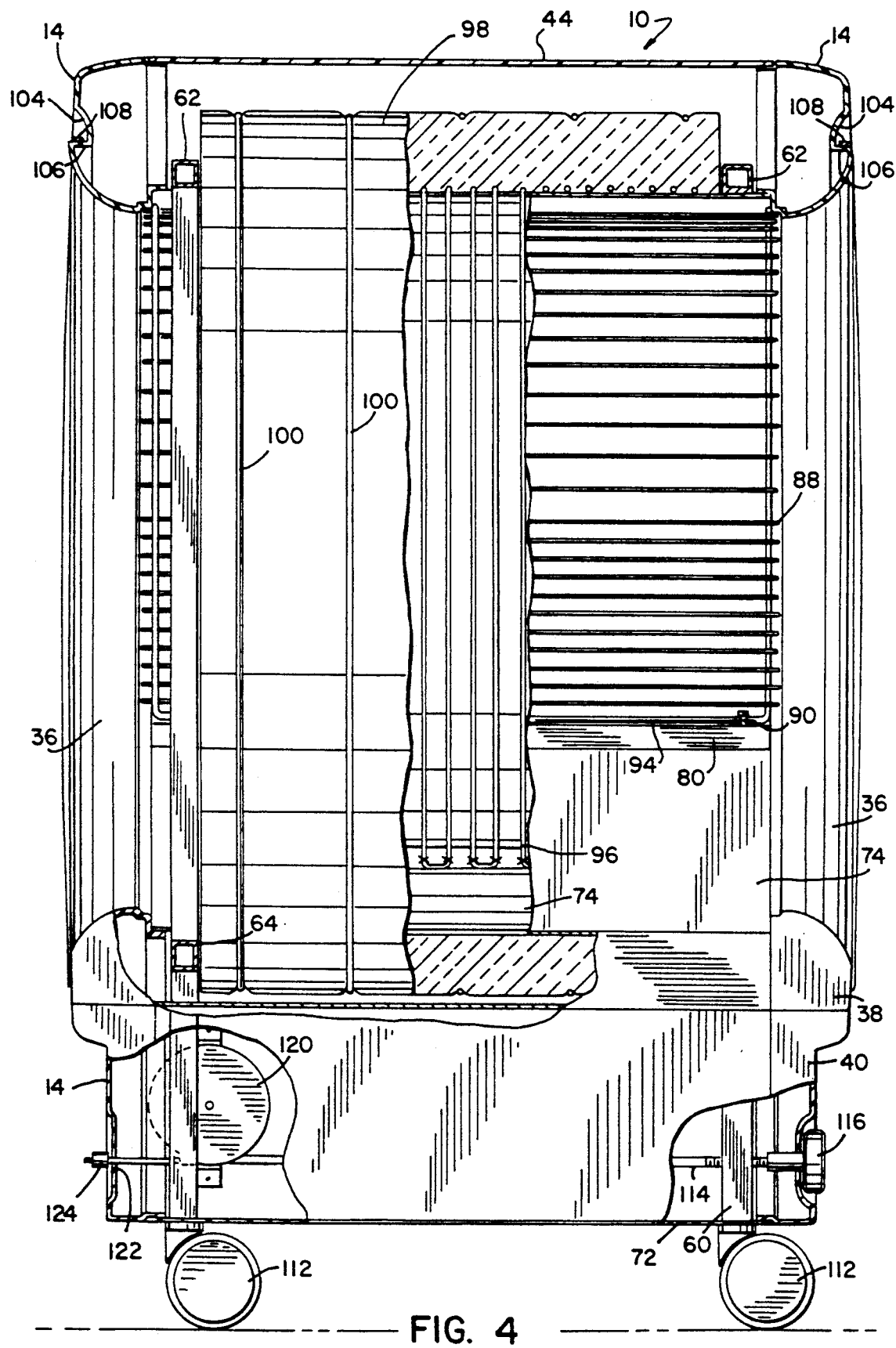
FIG. 4 is a section view looking in one direction of arrow 4—4 of FIG. 2.

As best shown in FIGS. 2 and 4, the end walls 14 and panels 42, 44 are secured to and carried by a structural frame 58 having uprights or partial standards 60, an upper cross brace 62 and a lower cross brace 64. Reinforcing braces such as the angle brace 66 provide structural rigidity to the frame. A longitudinal brace 68 secures the front and back frame members 58 to one another adjacent either side of the slot 38, as best illustrated in FIG. 2. The longitudinal brace 70 is provided adjacent each top cross brace 62 for securing the front and back top braces of the frames 58 to one another near the top panel 44. In the preferred embodiment, the frame is of a unitary welded construction, but it will be readily understood by those who are skilled in the art that any suitable method of assembly may be used. A pair of bottom panels 72 are secured to each of the cross bases 64 and uprights 60 to provide a closure for the rectangular slotted portion 40 of the key hole opening 16, as best seen in FIGS. 1 and 2.

The end panels 14, side panels 42, top panel 44 and insert panels 50 are secured to the frame 58 to skirt and enclose the entire heating unit. In the preferred embodiment, the end panels 14 are each made of a molded fiberglass construction. The top panel 44, side panels 42 and bottom panels are of formed stainless steel or the like. The entire outer surface is covered with an enamel to enhance its aesthetics as well as to provide a relatively impenetrable, easy to clean surface.

A slotted, cylindrical, stainless steel drum 74 is mounted on the frame as shown in FIG. 2 and is typically bolted to the frame with one bolt (not shown) in each of the frame braces it touches. In the preferred embodiment, an insulating material such as, by way of example, the insulating washer carried by each bolt may be disposed between the frame braces and the drum 74 to isolate the drum from the frame and the remainder of the unit. In the preferred embodiment, the drum is made of Type 304 stainless steel, with a sand blasted finish, to provide an efficient radiant heating transfer device for defining the radiant heating chamber 78 of the subject invention.

As best seen in FIGS. 2 and 6, an elongate rail 80 is secured to the drum 74 by securing the rail 80 to the drum using one or more fasteners as 84 or the like. A rail is mounted on the drum of either side of and above the slot 38. Each rail 80 includes a linear axially extending track portion 85. A wire grid 88 is placed inside the heating chamber 78 and is held in place, spaced outwardly from the drum, by placing the longitudinally extending end edges 94 on tracks 88. The wire grid 88 is coated with a heat resistive coating, such as a plastimeric PVC coating, and is spaced outwardly from the surface of the drum 74 to keep the patient from coming into contact with the hot surface of the drum during treatment. The wire grid held in position on the rails 86 by a plurality of pins 90 which are maintained in suitable openings or apertures 92 in support 82 which is suitable attached to the rail 80, as shown in FIGS. 4 and 6. The side edge 86 of the extended rail 80 projects into the chamber to limit side-to-side movement of the stretcher 12 as it is moved into and out of the unit. The outer or lower edges 94 of the grid 88 are above the slotted portion 38 of the unit opening but, as can be seen in FIGS. 2 and 6, are all times below the pad 20 and the upper surface of bed 26 of the stretcher, assuring that the patient cannot come into contact with the drum 74.

Figure 3:
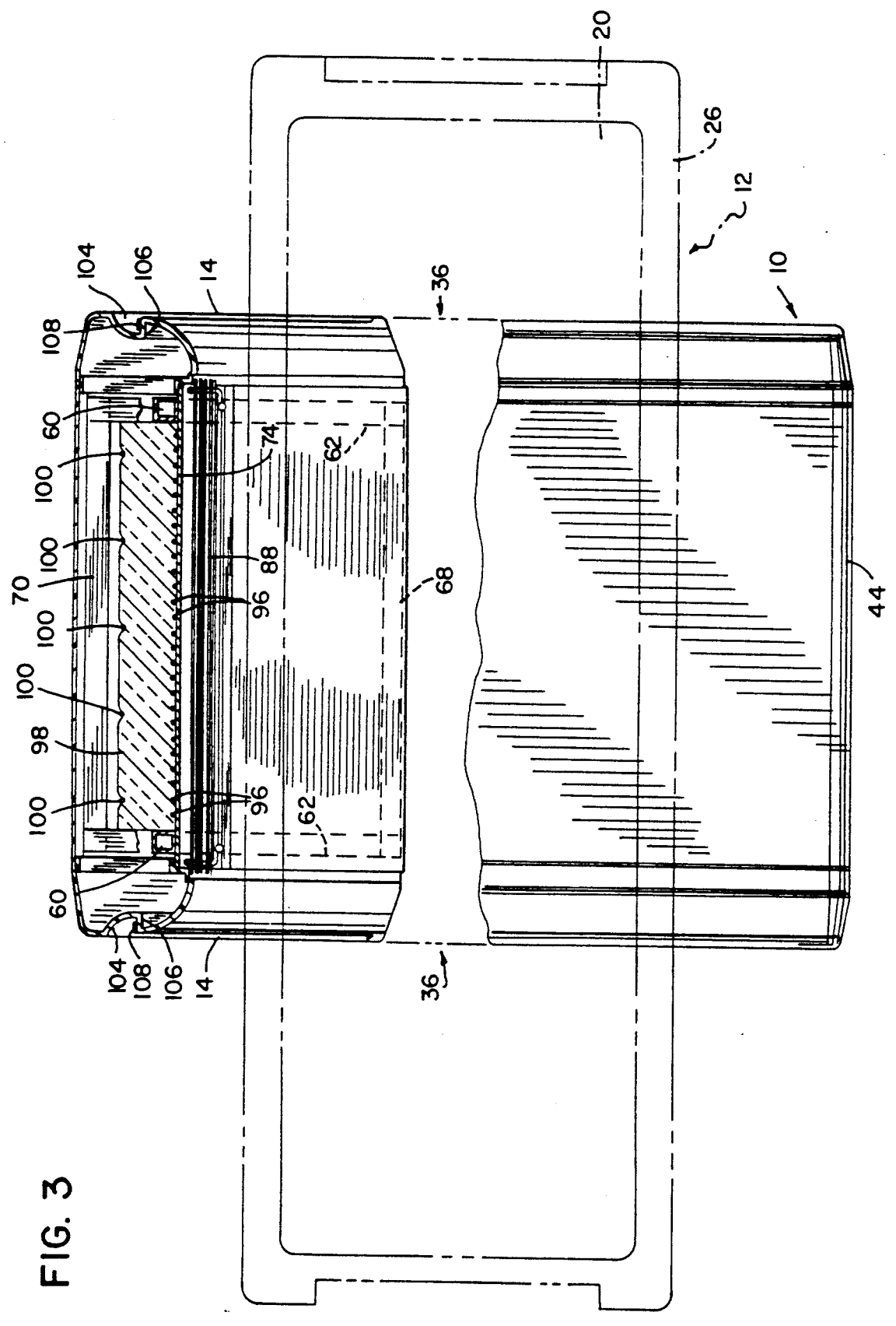

With specific reference to FIGS. 3 and 4, it will be noted that the exterior surface of the drum has in contact therewith a continuous heating coil 96 disposed in a plurality of parallel, spaced apart rows extending from one longitudinal edge of the slotted drum cylinder about the periphery of the drum to the other longitudinal edge of the drum. In the preferred embodiment, the heating coils are insulated 450° C. high temperature cable manufactured by Harbour Industries, and are mounted in direct contact with the drum. The heating coils may be secured directly to the drum by a plurality of means. However, tape such as, by way of example, extreme high temperature tape, manufactured by Custom Tapes, Inc., has been found to be suitable for this purpose.

As is best shown in FIG. 4, an insulation pad such as, by way of example, 1000° 1½" fiberglass insulation, manufactured by Owens-Corning, is placed over the heating coils and held securely against the drum by a series of straps 100. The insulation pad protects the outer skirt of the unit from heat and increases the efficiency of the unit by directing the heat generated by the heating coils 96 into the drum 74.

The enlarged circular opening 36 of the key hole 16 includes a rim or lip 102, as best shown in FIGS. 1 and 5. The outer edge of the lip 102 includes an integral channel 104 having a track or continuous edge 106 which is parallel to the axis of the drum 74. In the preferred embodiment, a VELCRO fastener strip 108 is secured to the track 106. The mated VELCRO fastener strip 109 is secured to one edge of a thermal blanket 110, whereby the thermal blanket may be fastened to the unit for closing the openings 36 around the patient during treatment to contain the heat within the confines of the heating chamber 78. In the preferred embodiment, the fasteners are Velcro brand hook and loop fasteners. The thermal blanket is an Astrocon No. 8 foil-backed nylon sheet, manufactured by Metalized Products.

As best shown in FIGS. 2 and 4, a plurality of rollers or casters 112 may be mounted in the ends of the upright standards or braces 60 of the frames 58 to provide for portability of the unit. In the preferred embodiment, a locking bar 114 is secured to the front and back braces and is engageable with the wheels to selectively lock the unit against movement. The locking bar is operable by means of a turning knob 116 which extends through an end panel 14 of the unit. The unit can be locked in place against accidental movement simply by turning each of the knobs 116 in one direction and unlocked by turning the knobs in the opposite direction.

A typical power and control circuit for the subject invention is shown in FIG. 7. The unit is designed to be used with standard 120 volt AC power as indicated by the power supply symbol 118. In the preferred embodiment, the power cord is in a recoil reel assembly 120, as shown in FIGS. 2 and 4. The power cord extends through a suitable opening 122 provided in an end panel 14 of the unit and includes an integral plug 124 which may be plugged into a standard wall receptacle. The power lines 126 and 128 are mounted in suitable manner to the upright brace or standard 60 of the frame and extend to the control module 130 of the unit, as shown in FIG. 2. The control module 130 is mounted in an inset panel 50 and includes the thermostat 132, the relay 134, the bi-metal safety interrupt 136, and the on/off switch 138. In the preferred embodiment, one side of the power supply 118 is interrupted by the switch 138 and is attached via the line 140 to the thermostat 132. The thermostat is in direct communication with a sensor 142 which is mounted in the top of the drum, near the top, center of the chamber, as shown in FIG. 2. The sensor senses the heat in the chamber and communicates a correlating signal to the thermostat via lines 144 and 146. The thermostat is in direct communication with an electronic control relay 134 via lines 148 and 150. When the heat level in the chamber is below that programmed into the thermostat, the relay is operative to close the circuit between the power supply 118 and the heating coils 96 to provide power thereto for providing a resistance heating of the coils to heat the drum 74. The thermostat and relay operate in the well known manner to disengage the power supply from the heating coils when the sensor indicates that the temperature of the chamber has reached the programmed temperature of the thermostat. In the preferred embodiment, the sensor 112 is a 100 ohm platinum film sensor, manufactured by Gordon Company, and the thermostat is an EWPC/800 electronic thermostat, manufactured by Eliwell-U.S.A. A bi-metal safety interrupt such as, by way of example, the 250° F. bi-metal thermostat, manufactured by Bimet Corp., is inserted in series between the heater 96 and the relay 134 to insure against accidental overheating of the drum 74 if the sensor and/or thermostat malfunctions for any reason.

In typical operation, a thermal recovery patient will be placed on the stretcher 12, as shown in FIG. 1. The stretcher will then be nested in the heating chamber of the unit, as shown in FIGS. 2 and 3, with the upper body portion of the patient inside the chamber 80. The blankets 110 are then draped over the patient to close the chamber 80. Power is turned on by closing switch 138 and the heating coils are operative to bring the chamber temperature to approximately 105° F. The patient is maintained in this environment until his core body temperature reaches the desired level. Using the radiant heating techniques of the present invention, the patient's body core temperature is elevated without undue stress to or localized heating of the skin. This treatment is particularly suited for patients suffering from environment induced hypothermia as well as for recovery from lowered body temperatures induced for certain medical procedures.

While certain features and embodiments of the invention have been disclosed herein, it will be readily understood that the invention includes all modifications and enhancements within the scope and spirit of the appended claims.

I claim:

1. A radiant heating device for treating a patient in a treatment area having a floor, said device, comprising:
   an enclosure resting on the floor, said enclosure having an interior surface and defining a chamber for accepting and surrounding at least a portion of the body of the patient to be treated;

a pair of opposite, open ends in said enclosure, each of said open ends being adapted to receive a self-supporting mobile patient support member also resting on the floor;

a heater that heats the interior surface of said enclosure; and a guard attached to said enclosure and spaced outwardly from said interior surface, that prevents direct contact of said interior surface by said patient during treatment, said guard including a grid through which radiant heat passes.

2. The radiant heating device of claim 1, wherein said patient is exclusively supported by said mobile patient support member during treatment.

3. The radiant heating device of claim 1, wherein said enclosure includes a drum made from a thermally-conductive material, and wherein said heater includes resistance heating coils in direct contact with said enclosure for supplying heat to said enclosure.

4. The radiant heating device of claim 3, further including an insulating pad placed over said enclosure and over said resistance heating coils.

5. The radiant heating device of claim 4, wherein the insulating pad includes fiberglass.

6. The radiant heating device of claim 1, further comprising:

a removable closure means on each of said open ends of said enclosure for closing said open ends of said chamber during treatment.

7. The radiant heating device of claim 6, wherein said closure means comprises:

a pair of flexible thermal blankets, each of said blankets being draped over its respective open end and/or over the body of said patient during treatment.

8. The radiant heating device of claim 7, wherein said closure means further comprises:

removable fastener assemblies secured to said enclosure and to each of said thermal blankets, whereby the blankets may be selectively secured to and removed from said enclosure.

9. The radiant heating device of claim 8, wherein each of said removable fastener assemblies include a hook and loop fastener having a hook member and a loop member.

10. The radiant heating device of claim 1, wherein said heater is adapted to maintain a chamber temperature of approximately 105° F.

11. The radiant heating device of claim 10, wherein said guard includes an outer surface coating that maintains the temperature of the outer surface of said guard surface at approximately 105° F.

12. The radiant heating device of claim 11, wherein said surface coating includes polyvinyl chloride.

13. The radiant heating device of claim 11, wherein said guard is removably secured to the interior surface of said enclosure.

14. The radiant heating device of claim 11, further comprising:

a sensor that senses the temperature in said chamber; and means associated with said sensor and said heater for selectively engaging and disengaging said heater in response to the sensed temperature of the chamber.

15. The radiant heating device of claim 14, further comprising:

a safety interrupt means for disengaging said heater when the chamber temperature exceeds a predetermined level.

* * * * *